US005787883A

United States Patent [19]

Cramer

[11] Patent Number: 5,787,883
[45] Date of Patent: Aug. 4, 1998

[54] SPRING-FREE PRESSURE REGULATOR WITH STRUCTURE ISOLATING EXHALED AIR FROM VALVE

[75] Inventor: Robert L. Cramer, Davenport, Iowa

[73] Assignee: Litton Systems, Inc., Davenport, Iowa

[21] Appl. No.: 376,084

[22] Filed: Jan. 20, 1995

Related U.S. Application Data

[63] Continuation of Ser. No. 70,555, Jun. 1, 1993, abandoned.

[51] Int. Cl.[6] .......... F16K 31/12; F16K 31/26; A61M 16/00; A62B 7/04

[52] U.S. Cl. .......... 128/205.24; 128/204.26; 137/505; 137/505.2

[58] Field of Search .......... 128/201.27, 201.28, 128/204.26, 205.11, 205.12, 205.22, 205.24, 205.13–205.17, 205.27, 205.28

[56] References Cited

U.S. PATENT DOCUMENTS

| | | | |
|---|---|---|---|
| 3,952,773 | 4/1976 | Hahn | 128/204.25 |
| 4,186,735 | 2/1980 | Henneman et al. | 128/201.25 |
| 4,299,216 | 11/1981 | Bernard et al. | 128/205.12 |
| 4,334,532 | 6/1982 | Jackson | 18/204.26 |
| 4,337,766 | 7/1982 | Feathers | 128/204.26 |
| 4,498,470 | 2/1985 | Warncke | 128/202.26 |
| 4,606,340 | 8/1986 | Ansite | 128/205.24 |
| 4,640,277 | 2/1987 | Meyer | 128/204.23 |
| 4,682,591 | 7/1987 | Jones | 128/204.25 |
| 4,750,485 | 6/1988 | Bartos | 128/204.26 |
| 4,774,942 | 10/1988 | Moellers | 128/205.24 |
| 4,856,507 | 8/1989 | Ouillon et al. | 128/204.29 |
| 4,879,998 | 11/1989 | Moellers | 128/205.24 |
| 5,036,841 | 8/1991 | Hamilton | 128/205.17 |

FOREIGN PATENT DOCUMENTS 799635 8/1958 United Kingdom .

*Primary Examiner*—Kimberly L. Asher
*Attorney, Agent, or Firm*—Scott J. Coonan; Gerald L. Lett

[57] ABSTRACT

A gas mixing pressure regulator for a closed circuit breathing apparatus comprises a first inlet to provide pressurized air to the breathing apparatus, a pressure responsive demand valve for opening and closing a first inlet, a second inlet for supplying carbon dioxide-free exhaled air from the breathing apparatus, and a mixing chamber for mixing the pressurized air and exhaled air for supplying breathable air to the breathing apparatus. The demand valve is isolated from the mixing chamber by a check valve injector nozzle to prevent contamination thereof and is responsive to pressure demands from the breathing apparatus to ensure reliability, stability and long life.

9 Claims, 1 Drawing Sheet

SPRING-FREE PRESSURE REGULATOR WITH STRUCTURE ISOLATING EXHALED AIR FROM VALVE

This application is a Continuation of application Ser. No. 08/070,555 filed on Jun. 1, 1993, now abandoned.

FIELD OF THE INVENTION

This invention relates to a breathing apparatus for use in hazardous environments and more particularly to a gas mixing pressure regulator for supplying breathable gas to the breathing apparatus.

BACKGROUND OF THE INVENTION

It is generally known to use a breathing apparatus when working under hazardous conditions or environments such as fighting fires. A typical breathing apparatus generally comprises a face mask, a supply of pressurized oxygen/nitrogen mixture, an inhalation tube extending from the pressurized supply to the face mask, an exhalation tube that receives exhaled air which is then directed to an exhalation chamber and through a scrubber assembly to remove carbon dioxide from the exhaled air. The carbon dioxide-free air is then mixed with a proper mixture of oxygen/nitrogen and is recirculated back through the system as breathable air. Typically, a pressure regulator is provided for mixing the carbon dioxide-free exhaled air with the proper mixture of oxygen/nitrogen from the pressurized supply for recirculation back through the face mask as breathable air.

Prior pressure regulators required the use of mechanical springs for opening and closing valves for properly mixing gas from the pressurized supply and exhaled air. Such springs are subject to not only failure but energy loss and instability requiring the need for a by-pass in case of a malfunction. In the event of failure of the springs within the regulator, unregulated breathable air could flow from the pressurized supply directly to the face mask. Conversely, failure of the opposing spring can prevent flow of breathable gas to the mask. This latter condition must, by regulation, be prevented by an elaborate by-pass mechanism which this invention eliminates.

Another problem is that, in previous designs, a breathing diaphragm is biased against an external spring for moving an inlet for supplying pressurized air to the face mask. Such springs have been found to be unstable and tend to move away from the lever during exhalation causing a delay in the response to the need for breathable air by the user.

Yet another problem encountered with prior designs is that after each use the parts of the breathing apparatus exposed to exhaled air need to be cleaned. In prior devices, the sliding levers and valves were not isolated from the exhaled air and thus water vapor from the exhaled air as well as from cleaning solution contaminated the sliding levers and valves and thus adversely affected their operation leading to a delayed response or failure.

SUMMARY OF THE INVENTION

A pressure regulator for a breathing apparatus of this invention has a mixing chamber for providing a proper mixture of enriched stored oxygen/nitrogen gas and exhaled gas which has been scrubbed of carbon dioxide, a first inlet port to supply enriched stored gas to the mixing chamber, a second inlet port to supply carbon dioxide-free exhaled gas to the mixing chamber, and a mixing tube for supplying the mixed gases to a face mask. A pressure responsive demand valve is provided to open the first inlet to supply enriched stored gas to the mixing chamber. The pressure demand valve includes a sliding stem for opening and closing the first inlet port actuated by a pivotable lever in response to a pressure sensitive diaphragm. The valve is pneumatically isolated from the mixing chamber to prevent moisture from the exhaled air and cleaning solution from contaminating the valve.

Objects, features and advantages of this invention are to provide an improved pressure regulator for a breathing apparatus that does not utilize mechanical springs, eliminates the need for a by-pass, and utilizes a valve that is pressure responsive, in which the lever and sliding valve are isolated from contaminants and cleaning solution, is more efficient, is more reliable, rugged, stable, durable economical to manufacture and assemble and in service has a long useful life.

BRIEF DESCRIPTION OF THE DRAWINGS

These and other objects, features and advantages of this invention will be apparent from the following detailed description of the best mode, appended claims and accompanying drawings in which:

DETAILED DESCRIPTION

Figure 1:
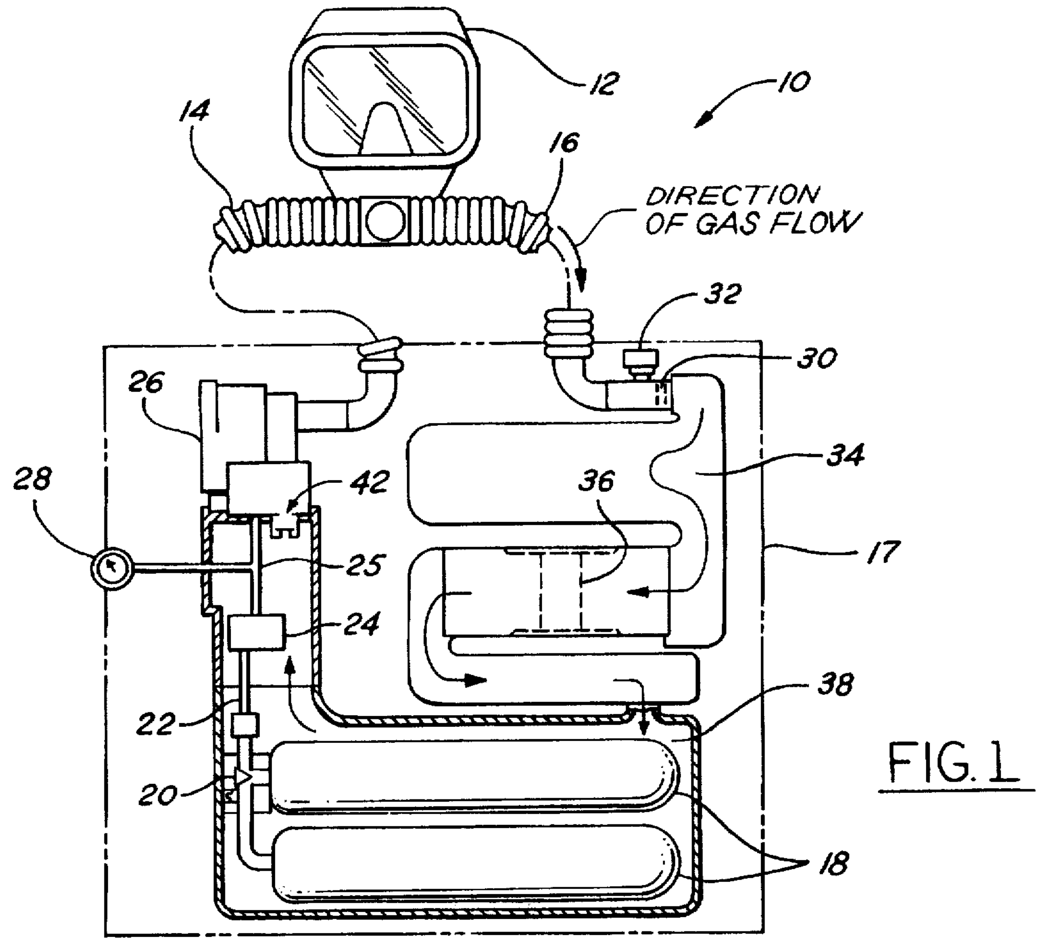
FIG. 1 is a schematic drawing of the breathing apparatus embodying the present invention.

Referring in more detail to the drawings, FIG. 1 illustrates a breathing apparatus 10 embodying this invention having a face mask 12, an inhalation tube 14 and an exhalation tube 16, both of which are connected to a breathable air supply contained within a carrier pack 17 which can be worn on the back of the user. The source of pressurized stored gas 18 is provided within the carrier pack 17 and contains an oxygen/nitrogen mixture, preferably at a ratio of 38% oxygen. The oxygen rich gas is supplied to the face mask 12 via an on/off valve 20, high pressure hose 22, pressure reducer 24, connector hose 25, pressure regulator 26, inhalation tube 14 and the face mask 12. A pressure indicator 28 is interposed via a T connection in connector hose 25. As the user breathes, exhaled air travels from the face mask 12 through the exhalation tube 16, an exhalation check valve 30 and into an exhalation chamber 34. A pressure relief valve 32 is provided for the exhalation tube. Exhaled air accumulates in the exhalation chamber 34 and eventually flows through a scrubber assembly 36 which removes carbon dioxide from the exhausted air. The scrubber 36 has opposed filter screens with a soda/lime mixture therebetween that chemically reacts with the carbon dioxide from the exhaled air to form calcium and sodium carbonate and thereby removes the carbon dioxide from the exhaled air. Thereafter the carbon dioxide-free and oxygen-poor exhaled air flows into a return chamber 38 and it is eventually returned to the pressure regulator 26 through a return port 40 having a return port check valve 42. The exhaled air is then mixed with the oxygen-rich gas from the supply 18 in the proper ratio to provide breathable air to the inhalation tube 14 and eventually to the user through the face mask 12. In use, the ratio of exhaled air to oxygen rich air is approximately 4 or 5 to 1.

Figure 2:
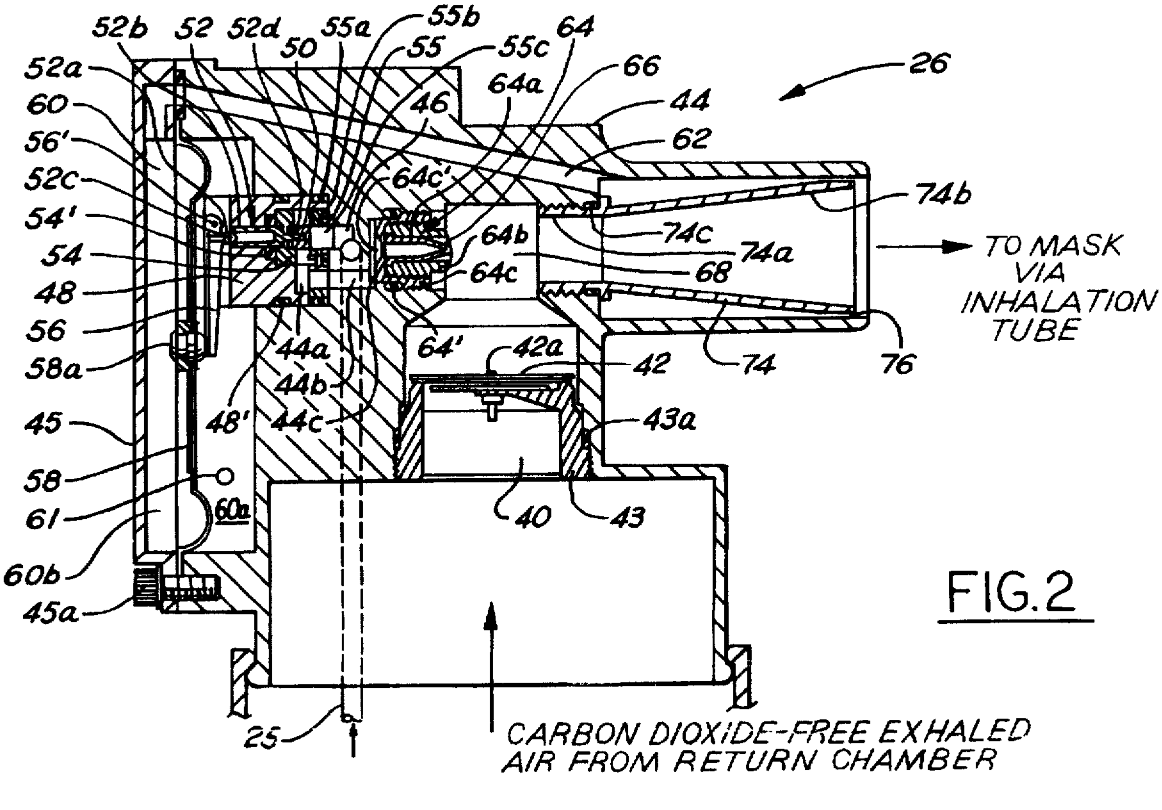
FIG. 2 is an enlarged cross-sectional view of the pressure regulator.

The regulator 26 both controls the flow of high pressure gas and mixes it with the carbon dioxide-free exhaled air to supply the resulting mixture of oxygen enriched air to the user of the apparatus 10 upon breathing demand of the user by inhaling and exhaling. As shown in FIG. 2, the regulator 26 has a demand diaphragm and valve assembly disposed in a chamber 60 for mixing the pressurized gas and exhaled air to produce oxygen enriched air to be supplied to the mask 12. The pressure regulator 26 has a housing 44 with a cover 45 secured thereto by any suitable means such as cap screws 45*a*. The housing 44 has a high pressure inlet 46 that receives pressurized gas through the hose 25 from the supply 18. A valve assembly bushing 48 has a poppet valve 50 for opening and closing the inlet 46 and is operated by a valve stem 52. A seal 48' is provided between the bushing 48 and the housing 44 to prevent air leakage. The valve stem 52 is formed by a stem 52*a* threaded into a sleeve 52*b* to the desired height and secured thereto by a thread locking patch 52*c*. The poppet valve 50 has a loose sliding connection with the sleeve 52*b* through the extension 52*d*. The valve stem 52 slides within the bushing 48 and a valve stem guide 54 provided in the bushing and sealed by seals 54' so that as the valve stem 52 reciprocates, the poppet valve 50 opens and closes. In normal operation, with on/off valve 20 in the on position and prior to any breathing by the user, poppet valve 50 is yieldably biased in the open position by the pressure of the gas from supply 18. A valve seat 55 is provided in the bushing 48 and is sealed by packing seals 55*a*, 55*b*. An opening 55*c* in the valve seat communicates with the inlet 46 to supply pressurized gas from the supply 18 to the face mask 12 upon opening of the poppet valve 50. The poppet valve 50 is opened and closed by a lever 56 pivotally mounted at one end to the bushing 48 by pins 56' and engaged at the opposite end by a diaphragm 58 through a button 58*a* secured thereto. Hence, lever 56, bushing 48, pins 56', and button 58*a* form means for operably connecting poppet valve 50 and diaphragm 58. The diaphragm 58 is clamped between the housing 44 and the housing cover 45 and is located in a pressure sensing chamber 60 formed between the housing 44 and the housing cover 45. One side 60*a* of the pressure sensing chamber 60 is maintained at ambient pressure through ambient port 61. The other side 60*b* of the pressure sensing chamber 60 is maintained at operating pressure (which is generally 1 inch of water or less) through a pressure sensing port 62 which communicates with the face mask 12.

Means are provided to isolate poppet valve 50 from mixing chamber 68 by preventing the flow of carbon dioxide-free air to valve 50. Housing 44, also contains a check valve assembly 64 which is connected to the high pressure inlet 46 by ports 44*a*, 44*b*, 44*c*. The assembly 64 comprises a silicon rubber check valve injector nozzle 64*a* press fit into a nozzle sleeve 64*b* that is threaded into an outer sleeve 64*c*. The outer sleeve 64*c* is threaded to the housing 44. Packing seals 64' prevent air loss around the assembly 64. In this way, check valve assembly 64 forms means for isolating poppet valve 50 from mixing chamber 68 by preventing the flow of exhaled air from mixing chamber 68 to poppet valve 50. The outer sleeve 64*c* has an opening 64*c'* communicating with the high pressure ports 44*a*, 44*b*, 44*c* to supply high pressure gas from the inlet 46 to the face mask 12. The flexible and flattened or conical end 66 of the nozzle 64*a* normally remains closed until high pressure gas from the inlet 46 flows through the nozzle 64*a* forcing the conical end 66 open so that the high pressure gas may flow to a mixing chamber 68. The open end of the nozzle sleeve 64*b* limits the opening of end 66 of the nozzle 64*a* to prevent damage thereto. Means are provided for limiting the opening of nozzle 64*a* in order to prevent damage thereto. Those means comprise the open end of the nozzle sleeve 64*b* which limits the opening of end 66 of the nozzle 64*a*, thereby ensuring the continued performance of nozzle 64*a*.

A silicon rubber flapper check valve 42 is mounted on a valve housing 43 by a pin 42*a*. The valve housing 43 is threaded into the housing 44 and packing seals 43*a* prevent air and pressure loss. The valve housing 43 forms the return port 40 for supplying carbon dioxide-free air to the mixing chamber 68.

A conical or flared mixing tube 74 is threaded at its narrow end 74*a* into the housing 44 adjacent the mixing chamber 68 and at its wide end 74*b* has an outer diameter forming a narrow passage 76 with the housing 44. Seals 74*c* are provided to prevent air and pressure loss. The inhalation tube 14 is connected to the housing 44 adjacent the end 74*b* to provide breathable air to the face mask 12.

In use, the face mask 12 is secured over the face of the user and the carrier pack 17 is strapped to the user's back as is known in the art. When turned to the on position, the on/off valve 20 supplies regulated pressurized gas of approximately 70–100 PSIG as controlled by the pressure reducer 24 through the hose 25 to the inlet 46. When the on/off valve 20 is in the off position, the pressure in the chamber 60 is at about 1 inch of water or less, biasing the diaphragm 58 against the lever 56 to close the valve 50. The pressure of the gas from the supply 18 is greater than that in the chamber 60. Thus, when the on/off valve 20 is turned on, increased pressure in the inlet 46 forces the valve 50 to open against the bias of the diaphragm 58 to allow the pressurized oxygen rich gas supply to flow from the inlet 46 via ports 44*a*, 44*b*, 44*c*, through the check valve injector nozzle 64, into the mixing chamber 68 and through the mixing tube 74 to the face mask 12 through the inhalation tube 14.

As the high pressure gas flows through the nozzle 64*a* into the mixing chamber 68, a venturi-like effect is produced where the high velocity of flow of the pressurized gas from the nozzle 64*a* causes a pressure decrease in the mixing chamber 68. The pressure decrease causes the flapper check valve 42 to open at the left side in FIG. 2 allowing carbon dioxide-free air to flow from the return port 40 into the mixing chamber 68 to mix with the pressurized gas from the supply 18. The mixed air then flows through the mixing tube 74 at a high velocity at the narrow end 74*a* and expands and slows in velocity as it flows toward the opposite flared end 74*b* allowing the pressurized gas and carbon dioxide-free air to further mix to form breathable air. The mixed breathable air then flows through the inhalation tube 14 to the face mask 12. As the user inhales, pressure in the face mask 12 and the inhalation tube 14 decreases. This decrease in pressure is sensed by the port 62 and thus reduces the pressure in chamber 60, allowing the gas pressure from the inlet 46 to open the valve 50 against the bias of the diaphragm 58. Air flow past the flared end 74*b* of the mixing tube 74 creates a venturi-like effect at the narrow passage 76 wherein the velocity of air flow past the passage 76 causes an additional pressure reduction at the port 62 and thus the chamber 60 to further assist in allowing the valve to open against the bias of the diaphragm 58.

Referring again to FIG. 1, as the user exhales, the exhaled air travels through the exhalation tube 16 and into the exhalation chamber 34. During exhalation, air within inhalation tube 14 is pressurized which increases the pressure sensed by the sensing port 62 and the diaphragm 58 in the pressure sensing chamber 60. When the pressure increases to approximately 1 inch of water or less, the diaphragm 58 is forced to the right (as viewed in FIG. 2), which pivots the lever 56 to close the valve 50 to shut off the flow of air from the high pressure hose 25. As the user again inhales, air in the inhalation tube 14 flows to the face mask 12 causing a pressure decrease initiating another inhalation cycle of the regulator.

In the pressure regulator 26, the poppet valve 50 functions without the use of any mechanical springs, eliminating the possibility of failure of the poppet valve 50, thus eliminating the need for a by-pass. The elimination of springs in the poppet valve 50 ensures faster response to pressure changes due to breathing demands of the user. Furthermore, the poppet valve 50 is isolated from the exhaled air by the check valve injector nozzle 64a which prevents the poppet valve 50 and lever from becoming contaminated by water vapor and cleaning solution.

What is claimed is:

1. A spring-free pressure regulator for a breathing apparatus having a source of stored gas and a supply of carbon dioxide-free exhaled air from the user of the apparatus, the pressure regulator comprising:

a body, a mixing chamber in said body for mixing the stored gas and the carbon dioxide-free exhaled air, a first inlet port communicating with said mixing chamber for supplying the stored gas to said mixing chamber, a second inlet port communicating with said mixing chamber for supplying the carbon dioxide-free exhaled air, a valve carried by the body, said valve communicating with said first inlet port and movable to an open position and a closed position to control the flow of stored gas to said mixing chamber, said valve being yieldably biased to the open position by the stored gas, means for pneumatically isolating said valve from said mixing chamber by preventing the flow of the exhaled air to said valve, a pressure sensing chamber operably connected to said valve and having an ambient side and a pressurized side responsive solely to pressure changes during inhaling by the user to open said valve to thereby discharge stored gas into said mixing chamber through said first inlet port and to pressure changes during exhaling by the user to close said valve to terminate the discharge of stored gas through said first inlet port, and an outlet carried by said body and communicating with said mixing chamber for supplying the mixture of stored gas and carbon-dioxide-free exhaled air to the breathing apparatus upon inhalation by the user.

2. A pressure regulator as defined in claim 1 wherein said pressure sensing chamber comprises a diaphragm located within said body forming an ambient chamber on said ambient side and a sealed chamber on said pressurized side, an ambient port in said body communicating said ambient chamber to the atmosphere and a pressure sensing port extending from said sealed chamber and adapted to communicate with the breathing apparatus so that the pressure in the sealed chamber is pressure controlled by and increases and decreases in response to breathing by the user.

3. A pressure regulator as defined in claim 2 further comprising:

means in said ambient chamber for operably connecting said diaphragm to said valve.

4. A pressure regulator as defined in claim 1 further comprising:

a lever typically carried at one end thereof by said body and engaged at the other end thereof with said diaphragm, said lever engaging said valve between the one end and the other end thereof such that when pressure in the sealed chamber increases during exhalation by the user, said diaphragm pivots said lever about the one end thereof to close said valve, and when the pressure in the sealed chamber decreases upon inhalation by the user, said valve opens in response to the stored gas from said first inlet.

5. A pressure regulator as defined in claim 1, wherein said means for pneumatically isolating said valve and said mixing chamber are located within said first inlet port.

6. A pressure regulator as defined in claim 1 further comprising:

a check valve nozzle interposed between said first inlet port and said mixing chamber to allow fluid flow from said first inlet port to said mixing chamber only when said valve is opened.

7. A pressure regulator as defined in claim 6 further comprising:

a nozzle sleeve, said nozzle sleeve limiting the opening of said check valve nozzle to prevent damage thereto.

8. A pressure regulator as defined in claim 7 wherein said means for limiting comprises a nozzle sleeve surrounding said check valve nozzle, wherein said check valve nozzle has a flattened, tapered end and said nozzle sleeve has an inner opening of a diameter greater than the tapered end of said check valve nozzle.

9. A pressure regulator as defined in claim 6 wherein said check valve nozzle is constructed from a resilient material and has a tapered outlet end and an inlet of a greater diameter than said outlet.

* * * * *